United States Patent [19]
Ando et al.

[11] Patent Number: 5,086,062
[45] Date of Patent: Feb. 4, 1992

[54] ANTIALLERGY AND ANTIINFLAMMATORY BENZOXAZOLINONES

[75] Inventors: Kazuo Ando; Nobuko Asai; Fumitaka Ito, all of Chita; Takashi Mano, Handa; Masami Nakane, Nagoya; Kunio Satake, Handa; Kaoru Shimada, Okazaki, all of Japan

[73] Assignee: Pfizer Inc., New York, N.Y.

[21] Appl. No.: 529,971

[22] Filed: May 29, 1990

Related U.S. Application Data

[63] Continuation-in-part of Ser. No. 483,612, Feb. 12, 1990, abandoned.

[30] Foreign Application Priority Data

Feb. 28, 1989 [JP] Japan ................................. 1-47429

[51] Int. Cl.$^5$ ...................... A61K 31/42; C07D 263/58
[52] U.S. Cl. ..................................... 514/321; 514/375; 546/270; 548/221
[58] Field of Search ................. 548/221; 514/375, 321; 546/270

[56] References Cited

U.S. PATENT DOCUMENTS 4,835,166  5/1989  Kitaura et al. ..................... 514/339

FOREIGN PATENT DOCUMENTS 39818   11/1981  European Pat. Off. .
249407  12/1987  European Pat. Off. ............ 548/221
360566   3/1990  European Pat. Off. .
8201186  4/1982  PCT Int'l Appl. ................. 548/221
8501289  3/1985  PCT Int'l Appl. ................. 548/221

OTHER PUBLICATIONS

*The Scrip Leukotriene Report*, 1985, PJB Publications Ltd., pp. i-iii and 1-25.

Primary Examiner—Donald G. Daus
Attorney, Agent, or Firm—Peter C. Richardson; J. Trevor Lumb; Gregg C. Benson

[57] ABSTRACT

This invention relates to certain benzoxazolinones which inhibit lipoxygenase and/or cyclooxygenase enzymes. Such compounds are useful in inhibiting such enzymes, per se, and are useful in treating allergic and inflammatory conditions in a mammal. This invention also relates to methods of inhibiting lipoxygenase and/or cyclooxygenase in a mammal with such benzoxazolinones; methods of treating an allergic condition in a mammal with such compounds; methods of treating an inflammatory condition in a mammal with such compounds; and pharmaceutical compositions comprising the benzoxazolinones hereof.

22 Claims, No Drawings

ANTIALLERGY AND ANTIINFLAMMATORY BENZOXAZOLINONES

CROSS REFERENCE TO RELATED APPLICATION

This application is a continuation-in-part of co-pending application Ser. No. 07/483,612, filed Feb. 22, 1990, now abandoned.

BACKGROUND OF THE INVENTION

This invention relates to benzoxazolinones. More specifically, this invention relates to certain benzoxazolinone compounds substituted not only at the 6-position with an amino side chain but also at the 4-, 5- or 7-position of the benzo-ring. Such compounds inhibit the action of lipoxygenase and/or cyclooxygenase enzymes and are useful as inhibitors of those enzymes, per se. The compounds of this invention are also useful in the treatment of a variety of allergic and inflammatory conditions in mammals. This invention also relates to pharmaceutical compositions comprising such benzoxazolinone compounds.

European patent application, published Dec. 16, 1987 under No. 249407, discloses benzoxalone compounds having an alkylamino group at the 6-position, which are lipoxygenase and/or cyclooxygenase inhibitors.

SUMMARY OF THE INVENTION

This invention provides novel benzoxazolinone compounds of the formula:

$$R-(Alk)-NH-\text{[benzoxazolinone]}-R_1 \quad (I)$$

or a pharmaceutically-acceptable acid addition salt thereof, wherein Alk is a $C_n$ straight or branched chain divalent alkyl group; n is 0, 1, 2, 3, 4 or 5;

$R_1$ is $(C_1-C_3)$alkyl or $(C_1-C_3)$alkoxy, $(C_1-C_3)$alkylthio, hydrogen, halo, phenoxy, phenylthio or trifluoromethyl; and R is selected from the group consisting of:

(a) [structure with $R_3$, X, $R_2$ on a ring with positions 1-6]

wherein $R_2$ and $R_3$ are each, independently, H, $(C_1-C_4)$alkyl, $(C_1-C_4)$alkoxy, $(C_1-C_4)$alkylthio, or halo, X is methylene which is unsubstituted or substituted with one methyl group, nitrogen which is unsubstituted or substituted with a protecting group, oxygen, sulfur, sulfoxide or sulfone, and the dotted line between the 2- and 4- positions represents an optional bond between positions 2 and 3 or positions 3 and 4;

(b) [three ring structures with A and B]

wherein A and B are each, independently, O or S;

(c) [naphthalene, tetralin, indane, chromane, and related structures]

(d) [bicyclic and oxabicyclic structures with $R_4$, $R_5$, and $(CH_2)_t$, $(CH_2)_p$]

wherein $R_4$ and $R_5$ are each, independently, H or $(C_1-C_4)$alkyl, p is 0, 1 or 2 and t is 0, 1 or 2 provided that the sum of p plus t equals 1 or 2; and the wavy line indicates that the moiety containing such wavy line can be endo- or exo-7-oxabicyclo[2,2,1]heptan-1-yl; and (e) $CH_3-(CH_2)_m-Y-$ wherein m is an integer from 1 to 3 and Y is oxygen, sulfur, sulfoxide or sulfone.

The term "halo" as used herein means fluoro, chloro, bromo or iodo. The term "nitrogen protecting group" as used herein means t-butoxycarbonyl, benzoyloxycarbonyl, acetyl or formyl.

A preferred group of compounds are those wherein n is 0 or 1, $R_1$ is halo, R is a member selected from Group (a). Especially preferred are those wherein $R_1$ is 5-fluoro and X is oxygen.

A second preferred group of compounds are those wherein n is 1, $R_1$ is halo and R is a member selected from Group (c). Especially preferred are those wherein $R_1$ is 5-fluoro.

A third preferred group of compounds are those wherein n is 1, $R_1$ is $(C_1-C_3)$alkyl, and R is a member selected from Group (a). Especially preferred are those wherein $R_1$ is 5-ethyl and X is oxygen.

A fourth preferred group of compounds are those wherein n is 1 and R is a member selected from Group (d). Especially preferred are those wherein $R_1$ is 5-fluoro.

A fifth preferred group of compounds are those wherein $R_1$ is halo and R is a member selected from Group (e). Especially preferred are those wherein $R_1$ is 5-fluoro, m is 1 and Y is oxygen.

A sixth preferred group of compounds are those wherein $R_1$ is $(C_1-C_3)$alkoxy and R is a member selected from Group (a). Especially preferred are those wherein $R_1$ is methoxy, n is 1 and X is oxygen.

The compounds of formula (I) may contain an asymmetric center, and therefore may exist as a pair of enantiomers. This invention is to be considered as embracing each pure enantiomer thereof, the racemates thereof and a mixture of the enantiomers thereof, partially or completely optically resolved.

The pharmaceutically-acceptable acid addition salts of the compounds of the formula (I) are those formed from acids which form non-toxic acid addition salts, for example, the hydrochloride, hydrobromide, sulfate or bisulfate, phosphate or acid phosphate, acetate, citrate, fumarate, gluconate, lactate, maleate, succinate, tartrate, methanesulfonate, benzene sulfonate, toluenesulfonate, and formate salts.

This invention includes pharmaceutical compositions for treatment of allergic inflammatory conditions in a mammal which comprise a pharmaceutically-acceptable carrier or diluent and a compound of formula (I) or a pharmaceutically-acceptable acid addition salt thereof. This invention also includes a method for treating an allergic or inflammatory condition in a mammal, especially man, which comprises administering to said mammal an antiallergy or antiinflammatory effective amount of a compound of formula (I) or a pharmaceutically-acceptable acid addition salt thereof.

Also embraced by the present invention is a method of inhibiting the action of the lipoxygenase enzyme as well as the action of the cyclooxygenase enzyme in a mammal in need thereof, which comprises administering to such mammal a lipoxygenase enzyme and/or cyclooxygenase enzyme inhibiting amount of a compound of formula (I) or a pharmaceutically-acceptable acid addition salt thereof. This invention also includes pharmaceutical compositions for inhibiting the action of lipoxygenase enzyme and/or cyclooxygenase enzyme in a mammal which comprise a pharmaceutically-acceptable carrier and a compound of formula (I) or a pharmaceutically-acceptable acid addition salt thereof.

DETAILED DESCRIPTION OF THE INVENTION

The novel compounds of formula (I) may be prepared by the following reaction scheme:

In the above formulae, Alk; R; and $R_1$ are as previously defined and n is 0, 1, 2, 3 or 4. In the first step, approximately equimolar amounts of the reactants, amine (II) and aldehyde (III) are combined in a suitable organic solvent. While the reaction is preferably conducted at ambient temperature, higher temperatures, for example, reflux, can be used without any significant disadvantages. Suitable organic solvents include $(C_1-C_4)$alkanol (e.g., methanol or ethanol), benzene, toluene and tetrahydrofuran. It may be advantageous to use a dehydrating agent. Molecular sieves are a preferred dehydrating agent. Optionally, a small amount of lower alkanoic acid such as acetic acid is added to catalyze the reaction. The reaction is essentially complete within 24 hours. The product of the formula (IV) can be isolated and purified by conventional procedures, e.g. recrystallization or chromatography, when the resulting imine is conjugated with an unsaturated group. It is, however, more convenient not to isolate this product but to subject it (i.e., in situ) to reaction conditions of the second step.

The second step of the reaction involves reduction of the C=N double bond by reaction with an appropriate hydrogen source. While the reduction may be carried out by employing a wide variety of reducing agents which are known to reduce a carbon-nitrogen double bond, the preferred method of this invention employs a metal hydride reagent or catalytic hydrogenation reaction. The hydride reagents suitably employed in this reaction include sodium borohydride, sodium cyanoborohydride and lithium cyanoborohydride. Typically, the reduction is carried out at ambient temperature, with an excess of the hydride reagent in $(C_1-C_4)$alkanol such as methanol or ethanol. A catalytic hydrogenation reaction employs a catalytic amount of a noble metal catalyst such as Pd/C or $PtO_2$ under hydrogen atmosphere. When the reduction is substantially complete, the desired product of formula (I) is isolated by standard methods. Purification can be achieved by conventional means, such as recrystallization or chromatography.

Certain compounds of formula (I) wherein n is 0 and R is a member selected from Group (a) are also obtained substantially in a similar manner to the process described above. However, for this group of compounds the process requires a ketone instead of aldehyde (III). Preferably, the required ketone can be any one of the following:

(VI) (VII)

where X is methylene which is unsubstituted or substituted with one methyl group, nitrogen which is unsubstituted or substituted with a protecting group, oxygen or sulfur and $R_2$ and $R_3$ are as defined above. For example, coupling of the compound (II) and the ketone (V) yields the imine of formula (VIII).

(VIII)

The latter compound is readily reduced to the desired compound (I). Convenient conditions for the above two-step conversion are not significantly different from those employed with the synthesis of compounds (I) where n is other than 0.

Compounds of formula (I) wherein R is a member of Group (a) wherein X is sulfoxide or sulfone; or R is a member of Group (e) wherein Y is sulfoxide or sulfone are prepared by oxidation of the corresponding compounds wherein X and Y are sulfur. The unoxidized compounds are prepared as described above. Suitable oxidation conditions include, but are not limited to, reaction of such compounds with alumina supported sodium metaperiodate in a suitable solvent such as ($C_1$–$C_3$)alkanol and/or tetrahydrofuran.

The olefinic products of formula (I), i.e., those having an optional double bond between the 2- and 4-positions of the R radical are themselves active inhibitors of LO/CO enzymes and also serve as intermediates for preparation of the corresponding reduced compounds of the formula:

(IX)

A particularly preferred method for such reduction comprises hydrogenating a compound of formula (I) to be reduced under hydrogen in the presence of a noble metal catalyst in a suitable solvent. Suitable solvents for this hydrogenation are, for example, diethyl ether, etrahydrofuran, dioxane, ethyl acetate and ($C_1$–$C_3$)alkanol such as methanol or ethanol. The noble metal catalysts used are known in the art, for example, nickel, palladium, platinum and rhodium. Particularly preferred agents are platinum oxide and palladium on carbon. A platinum catalyst is sometimes more preferred because it is not readily poisoned by sulfur. This hydrogenation requires low hydrogen pressure (1 to 4 atm) and runs at ambient temperature. When the hydrogenation is complete (from about 2 hours to 24 hours), the catalyst is removed by filtration and the product of formula (IX) is then isolated and purified, if desired, by a conventional method.

6-Aminobenzoxazolin-2-ones (II) are prepared by a variety of methods known in the art and illustrated in the Preparations hereinbelow. The aldehydes or ketones required for the above syntheses are available commercially, or by preparation according to literature methods.

The pharmaceutically-acceptable salts of the novel compounds of the present invention are readily prepared by contacting said compounds with a stoichiometric amount of an appropriate mineral or organic acid in either aqueous solution of in a suitable organic solvent. The salt may then be obtained by precipitation or by evaporation of the solvent.

The compounds of this invention inhibit the activity of the lipoxygenase and/or cyclooxygenase enzymes. This inhibition has been demonstrated by an assay using rat peritoneal cavity resident cells which determines the effect of said compounds on the metabolism of arachidonic acid.

In this test some preferred compounds indicate low IC50 values, in the range of $0.5\mu$ to 30 $\mu M$, with respect to both lipoxygenase/cyclooxygenase inhibitions.

The ability of the compounds of the present invention to inhibit lipoxygenase and/or cyclooxygenase enzymes make them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor, e.g., allergic bronchial asthma, skin disorders, rheumatoid arthritis, osteoarthritis and thrombosis.

The activity of the compounds of this invention can also be demonstrated in the standard carrageenin-induced rat foot edema test (C. A. Winter et al., Proc. Soc. Exp. Biol. III, p 544, 1962).

Thus, the compounds of formula (I) and their pharmaceutically-acceptable salts are of particular use in the treatment or alleviation of allergic or inflammatory conditions in a human subject as well in the inhibition of the cyclooxygenase and lipoxygenase enzymes.

For treatment of the various conditions described above, the compounds of formula (I) and their pharmaceutically-acceptable salts can be administered to a human subject either alone, or, preferably, in combination with pharmaceutically-acceptable carriers or diluents in a pharmaceutical composition, according to standard pharmaceutical practice. A compound can be administered by a variety of conventional routes of administration including orally, parenterally and by inhalation. When the compounds are administered orally, the dose range will be from about 0.1 to 20 mg/kg body weight of the subject to be treated per day, preferably from about 0.1 to 1.0 mg/kg per day in single or divided doses. If parenteral administration is desired, then an effective dose will be from 0.1 to 1.0 mg/kg body weight of the subject to be treated per day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of formula (I) and their pharmaceutically-acceptable salts can be administered, for example, in the form of tablets, powders, lozenges, syrups or capsules, or as an aqueous solution or suspension. In the case of tablets for oral use, carriers which are commonly used include lactose and corn starch. Further, lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solute should be controlled to make the preparation isotonic.

The present invention is illustrated by the following examples. However, it should be understood that the invention is not limited to the specific details of these examples Proton nuclear magnetic resonance spectra (NMR) were measured at 270 MHz unless otherwise indicated for solutions in perdeuterodimethyl sulfoxide (DMSO-$d_6$) and peak positions are expressed in parts per million (ppm) downfield from tetramethylsilane.

The peak shapes are denoted as follows: s, singlet; d, doublet; t, triplet; m, multiplet; br, broad.

EXAMPLE 1

5-Fluoro-6-[(5,6-Dihydro-2H-pyran-3-yl)methylamino]benzoxazolin-2-one

To a solution of 6-amino-5-fluoro-benzoxazolin-2-one (0.97 g, 5.7 mmole) and 3-formyl-5,6-dihydro-2H-pyran (0.71 g, 6.3 mmole) in ethanol (40 ml) were added molecular sieves (4A, 1 g). The mixture was heated under reflux for 3 hours. Upon cooling, the reaction mixture was filtered and the filtrate was concentrated to yield a solid product, which was washed with ethanol. This product was dissolved in methanol (200 ml) and then sodium borohydride was added in portions at room temperature. Stirring was continued for hours. The reaction mixture was concentrated and water was added. The organic material was extracted with ethyl acetate. The combined extracts were washed with brine, dried over magnesium sulfate, and concentrated. The resulting residue was recrystallized from methanol to afford 420 mg of the title product (28%): m.p. 175°–176° C.

IR (KBr): 1790, 1520, 1100, 960 cm$^{-1}$.

NMR: 2.03 (br, 2H), 3.61 (m, 4H), 3.97 (br, 2H), 5.53 (br, 1H), 5.74 (br, 1H), 6.68 (d, 1H), 6.90 (d, 1H), 11.23 (s, 1H).

EXAMPLES 2–7

In a like manner, employing the appropriate aldehydes (III) in the procedure of Example 1 afforded the corresponding compounds of formula (I).

R—(Alk)—NH—[benzoxazolin-2-one with $R_1$]

wherein Alk is $(CH_2)_n$

| Example No. | n | R | $R_1$ | m.p. (°C.) | IR(cm$^{-1}$) (Nujol) | NMR |
|---|---|---|---|---|---|---|
| 2 | 1 | (tetrahydrothiopyranyl) | F | 191–192 | 1770, 1520 | 2.22(br, 2H), 2.60(t, 2H), 3.02(br, 2H), 3.65(d, 2H), 5.61(br, 1H), 5.73(s, 1H), 6.65(d, 1H), 6.90(d, 1H), 11.22(br, 1H) |
| 3 | 1 | (dihydronaphthyl) | F | 224–225 (dec.) | 1780, 1650 1505 | 2.22(t, 2H), 2.74(t, 2H), 3.86(d, 2H), 5.77(br, 1H), 6.37(s, 1H), 6.68(d, 1H), 6.92(d, 1H), 6.95–7.10(m, 4H), 11.2(br, 1H) |
| 4 | 1 | (dihydropyranyl) | CH$_3$O— | | | |
| 5 | 1 | (dihydropyranyl) | CH$_3$CH$_2$— | | | (CDCl$_3$)2.04–2.12(2H, m)3.72–3.76 (2H, m), 4.08–4.14(2H, m), 5.79(1H, 2), 6.39(1H, s), 6.69(1H, s) |

EXAMPLES 2-7

In a like manner, employing the appropriate aldehydes (III) in the procedure of Example 1 afforded the corresponding compounds of formula (I).

[Structure: R—(Alk)—NH— attached to benzoxazolin-2-one with $R_1$ substituent]

wherein Alk is $(CH_2)_n$

| Example No. | n | R | $R_1$ | m.p. (°C) | IR(cm$^{-1}$) (Nujol) | NMR |
|---|---|---|---|---|---|---|
| 6 | 1 | [H$_3$C–CH(–)–CH$_2$–CH=C(CH$_3$)–CH(–)–O– ring, (cis)] | F | 180–182 | 1756 | (CDCl$_3$)1.25(d, J=6.3Hz, 3H), 1.34(d, J=6.8Hz, 3H), 2.00(br.s, 2H), 3.57–3.73 (m, 3H), 3.90(br.s, 1H), 4.30(br.s, 1H), 5.79(br.s, 1H), 6.60(d, J=7.1Hz, 1H), 6.80 (d, J=10.3Hz, 1H), 8.72(br.s, 1H) |

EXAMPLE 8

5-Fluoro-6-[(tetrahydro-4H-pyran-3-yl)propylamino]-benzoxazolin-2-one

To a solution of 6-amino-5-fluoro-benzoxazolin-2-one (2.1 g, 12.5 mmole) in methanol (80 ml) were added 3-(tetrahydro-2H-pyran-3-yl) propanal (1.95 g, 13.7 mmole) and acetic acid (1 ml) at room temperature, and then the mixture was stirred for 1 hour. Sodium cyanoborohydride (0.867 g, 13.7 mmole) was combined and stirring continued for 17 hours at room temperature. The reaction mixture was concentrated in vacuo, and the residue was treated with aqueous ammonium chloride solution. The organic substance was extracted with ethyl acetate/tetrahydrofuran. The extracts were washed with brine, dried over magnesium sulfate, and concentrated to afford crude product. This crude product was recrystallized from methanol to give 1.40 g of the title compound: m.p. 144°–145° C.

IR (KBr): 1770, 1090 cm$^{-1}$.

NMR: 1.00–1.30 (m, 3H), 1.38–1.63 (m, 5H), 1.75–1.85 (m, 1H), 2.91–3.03 (m, 3H), 3.20–3.28 (m, 1H), 3.73 (br.d, 2H), 5.13 (br, 1H), 6.73 (d, 1H), 6.89 (d, 1H), 11.21 (br, 1H).

EXAMPLES 9-33

In like manner, employing the appropriate aldehydes (III) or ketones (V)–(VII) in the procedure of Example 8 afforded the corresponding compounds of formula (I).

[Structure: R-(Alk)-NH- attached to benzoxazolin-2-one with $R_1$ substituent]

wherein Alk is $(CH_2)_n$

| Example No. | n | R | $R_1$ | m.p. (°C) | IR(cm$^{-1}$) (Nujol) | NMR |
|---|---|---|---|---|---|---|
| 9 | 0 | cyclohexyl | F | 200–202 | 3430, 1780, 1760 | 1.11–1.40(m, 5H), 1.58–1.72(m, 3H), 3.16–3.18(m, 1H), 4.71(d, 1H, J=7Hz), 6.89(d, 1H, J=10Hz), 11.21(br.s, 1H) |
| 10 | 1 | cyclohexyl | CH$_3$—CH$_2$ | 143–144 | 3480, 1960, 1905, 1850, 1760 | 0.89–0.98(m, 1905, 2H), 1.10–1.21(m, 5H), 2.43–2.50(m, 5H), 2.86–2.90(m, 2H), 3.30–3.32(m, 2H), 4.69(m, 1H), 6.47(s, 1H), 6.69(s, 1H), 10.98(br.s, 1H) |
| 11 | 1 | methylcyclohexyl | F | 170(dec) | 3460, 3220, 1775, 1750 | 0.90(d, 4H), 1.25–1.82(m, 5H), 2.18(s, 3H), 2.95(d, 1H, J=6Hz), 6.60(d, 1H, J=6Hz), 6.77(d, 1H), 8.06(br.s, 1H) |
| 12 | 0 | tetrahydropyran-3-yl | F | 220–221 | 3340, 1770 | 1.44(dd, 2H), 1.82(d, 2H), 3.28–3.52(m, 3H), 3.85(d, 2H), 4.93(dd, 1H), 6.88–6.92(m, 2H), 12.62(br.s, 1H) |

-continued

| Example No. | n | R | $R_1$ | m.p. (°C.) | IR(cm$^{-1}$) (Nujol) | NMR |
|---|---|---|---|---|---|---|
| 13 | 0 | (tetrahydropyran-yl, O in ring) | F | 204–205 | 1760, 1730 1660 | 1.42–1.70(m, 3H), 1.93(m, 1H), 3.18(dd, 1H, J=8.6, 11Hz), 3.68–3.82(m, 2H), 4.81(m, 1H), 6.88(d, 1H, J=7.3Hz), 6.90(d, 1H, J=11.0Hz) |
| 14 | 1 | (tetrahydropyran-yl) | F | 198–199 | 3450, 1780 | 1.17(d, 2H), 1.64(d, 2H), 1.82(m, 1H), 2.94(t, 2H), 3.25(d, 2H), 3.84(d, 2H), 5.25(m, 1H), 6.76(d, 1H), 6.88(d, 1H) |
| 15 | 2 | (tetrahydropyran-yl) | F | 191–192 | 1780, 1650 | 1.17(m, 2H), 1.45–1.62(m, 5H), 3.05(m, 2H), 3.82(dd, 2H, J=3.3, 10.6Hz), 5.12(m, 1H), 6.74(d, 1H, J=7.3Hz), 6.89(d, 1H, J=11.0Hz) |
| 16 | 1 | (dihydropyran-yl) | F | 110–112 | 3500, 1790 | 1.70–2.22(m, 4H), 3.19–3.33(m, 2H), 4.06(m, 1H), 4.23(m, 1H), 4.74(m, 1H), 6.40(d, 1H), 6.66(d, 1H), 6.79(d, 1H), 8.19(br.s, 1H) |
| 17 | 1 | (1,4-benzodioxan-yl) | F | 225(dec) | 1760, 1500 | 3.30–3.40(m, 2H), 4.01(dd, 1H), 4.33–4.40(m, 2H), 5.45–5.46(m, 1H), 6.80–6.95(m, 6H) |
| 18 | 2 | CH$_3$—CH$_2$—O— | F | 152–153 | 3480, 1790 1770, 1660 | 1.11(t, 3H, J=7.0Hz), 3.21(m, 2H), 3.45(q, 2H, J=7.0Hz), 3.52(t, 2H, J=6Hz), 5.03(m, 1H), 6.83(d, 1H, J=7.7Hz), 6.91(d, 1H, J=11Hz), 11.25(br.s, 1H) |
| 19 | 3 | CH$_3$—CH$_2$—O— | F | 127–128 | 3480, 1790 1770, 1660 | 1.11(t, 3H, J=7.0Hz), 1.77(m, 2H), 3.05–3.13 (m, 2H), 3.46–3.46(m, 4H), 5.21(br.s, 1H), 6.74(d, 1H, J=7Hz), 6.90(d, 1H, J=11Hz), 11.3(br.s, 1H) |
| 20 | 4 | CH$_3$—CH$_2$—O— | F | 66–67 | 3480, 1790 1770, 1660 | 1.22(t, 3H, J=7.1Hz), 1.72(m, 4H), 3.14(m, 2H), 3.45–3.54(m, 4H), 3.91(br.s, 1H), 6.62 (d, 1H, J=7Hz), 6.78(d, 1H, J=10Hz), 8.72 (br.s, 1H) |
| 21 | 5 | CH$_3$—CH$_2$—O— | F | 75–76 | 3480, 1790 1770, 1660 | 1.21(t, 3H, J=7.0Hz), 1.43–1.74(m, 6H), 3.11 (t, 2H, J=7.0Hz), 3.42–3.52(m, 4H), 3.79(br.s, 1H), 6.61(d, 1H, J=7.1Hz), 6.79(d, 1H, J=10Hz), 8.95(br.s, 1H) |
| 22 | 1 | (norbornyl ether, exo-) | F | 184–186 | 3450, 3380 1764, 1732 | 1.17–1.27(m, 1H), 1.35–1.62(m, 5H), 2.02–2.06 (m, 1H), 2.68–2.77(m, 1H), 2.84–2.96(m, 1H), 4.34(d, 1H, J=4.8Hz), 4.48(dd, 1H, J=4.4, 4.8Hz), 5.40(br.s, 1H), 6.72(d, 1H, J=7.3Hz), 6.89(d, 1H, J=10.6Hz), 11.21(s, 1H) |
| 23 | 1 | (norbornyl ether, endo-) | F | 192–194 | 3450, 1774 1650, 1628 1132, 1112 | 1.00(dd, 1H, J=5.1, 11.7Hz), 1.36–1.57(m, 3H), 1.73–1.89(m, 2H), 2.29–2.40(m, 1H), 2.98–3.06 (m, 2H), 4.41–4.49(m, 2H), 5.12(br.s, 1H), 6.82 (d, 1H, J=7.3Hz), 6.90(d, 1H, J=10.6Hz), 11.23(s, 1H) |
| 24 | 3 | CH$_3$S— | F | 137 | 1762 | 1.80(m, 2H), 2.05(s, 3H), 2.51(m, 2H), 3.11 (m, 2H), 5.25(m, 1H), 6.76(d, J=7.3Hz, 1H), 6.90(d, J=10.6Hz, 1H), 11.22(br.s, 1H) |
| 25 | 3 | CH$_3$(CH$_2$)$_3$O— | F | 99 | (KBr) 1780, 1520 1110 | (CDCl$_3$)0.93(t, 3H, J=7.3Hz), 1.32–1.46(m, 2H), 1.53–1.64(m, 2H), 1.92(tt, 2H, J=6Hz, 6Hz), 3.22(dt, 2H, J=6Hz, 6Hz), 3.44(t, 2H, J=6.4Hz), 3.57(t, 2H, J=6Hz), 4.34(br, 1H), 6.63(d, 1H, J=7.0Hz), 6.81(d, 1H, J=9.9Hz), 9.42(br, 1H) |
| 26 | 3 | CH$_3$(CH$_2$)$_3$S— | F | 100–101 | (CH$_2$Cl$_3$) 3470, 1780 | (CDCl$_3$)0.91(t, 3H, J=7.2Hz), 1.34–1.63(m, 4H), 1.93(m, 2H), 2.53(t, 2H, J=7Hz), 2.63(t, |

-continued

| Example No. | n | R | $R_1$ | m.p. (°C.) | IR(cm$^{-1}$) (Nujol) | NMR |
|---|---|---|---|---|---|---|
| | | | | | 1770, 1650 | 2H, J=7Hz), 3.26(br.s, 2H), 3.89(br.s, 1H), 6.52 (d, 1H, J=7.1Hz), 6.78(d, 1H, J=10.3Hz), 8.30(br.s, 1H) |
| 27 | 1 | bicyclic structure with O [[α]$_D^{20}$: +20.4° (c0.50, methanol)] | F | 189–190 | 3440, 3220 1760, 1744 1730, 956 | 1.18–1.63(m, 6H), 1.98–2.09(m, 1H), 2.68–2.77 (m, 1H), 2.85–2.96(m, 1H), 4.33(d, 1H, J=4.4Hz), 4.48(dd, 1H, J=4.4Hz, 4.8Hz), 5.39 (br, 1H), 6.72(d, 1H, J=7.7Hz), 6.89(d, 1H, J=10.6Hz), 11.21(s, 1H) |
| 28 | 1 | bicyclic structure with O [[α]$_D^{20}$: −20.4° (c0.50, methanol)] | F | 189–190 | 3440, 3220 1760, 1744 1730, 956 | 1.18–1.63(m, 6H), 1.98–2.09(m, 1H), 2.68–2.77 (m, 1H), 2.85–2.96(m, 1H), 4.33(d, 1H, J=4.4Hz), 4.48(dd, 1H, J=4.4Hz, 4.8Hz), 5.39 (br.s, 1H), 6.72(d, 1H, J=7.7Hz), 6.89(d, 1H, J=10.6Hz), 11.21(s, 1H) |
| 29 | 1 | bicyclic structure with O | F | 177–179 | 3460, 1762, 1652 | (CDCl$_3$)1.49(d, 1H, J=9.5Hz), 1.57–1.89(m, 5H), 3.37(d, 2H, J=5.9Hz), 3.61(d, 1H, J=7.0Hz), 3.69(dd, 1H, J=2.8Hz, 7.0Hz), 4.39 (br.s, 1H), 6.63(d, 1H, J=7.3Hz), 7.98(d, 1H, J=10.3Hz), 8.42(br.s, 1H) |
| 30 | 1 | tetrahydropyranyl-phenyl (cis) | F | 254–255 (dec.) | (KBr)1770, 1515, 945 | 1.56(br.d, 1H), J=11Hz), 1.98(br.d, 1H, J=7Hz), 2.17(dddd, 1H, J=13Hz, 13Hz, 13Hz, 4.5Hz), 3.17(br.d, 1H, J=13Hz), 3.25–3.36(m, 2H), 3.44–3.54(m, 2H), 3.99–4.09(m, 2H), 5.20 (br, 1H), 6.05(d, 1H, J=7.3Hz), 6.82(d, 1H, J=10.6Hz), 7.25–7.41(m, 5H), 10.4(br, 1H) |
| 31 | 1 | tetrahydropyranyl-phenyl (trans) | F | 199–200 | (KBr)1760, 1510, 950 | 1.62–1.86(m, 2H), 2.05–2.18(m, 1H), 2.48–2.58 (m, 1H, overlaid by solvent), 2.62–2.80(m, 2H), 3.17(dd, 1H, J=11Hz, 11Hz), 3.42(ddd, 1H, J=11Hz, 11Hz, 2Hz), 3.93(dd, 1H, J=11Hz, 3.3Hz), 4.11(dd, 1H, J=11Hz, 4Hz), 5.08(br, 1H), 6.17(d, 1H, J=7.3Hz), 6.84(d, 1H, J=10.6Hz), 7.22–7.39(m, 5H), 11.18(br, 1H) |
| 32 | 1 | bicyclic with O | F | 207–209 | 3440, 1772 1648, 1622 1520 | 1.22–1.78(m, 8H), 3.13(d, 2H, J=4.76Hz), 3.51 (dd, 1H, J=1.12Hz, 7.53Hz), 3.64(d, 1H, J= 7.35Hz), 4.22(t, 1H, J=5.36Hz), 5.06(br.s, 1H), 6.82(d, 1H, J=7.32Hz), 6.89(d, 1H, J=10.62Hz), 11.22(br.s, 1H) |
| 33 | 1 | dimethyl dioxolane structure (H$_3$C, H$_3$C, O, O) | F | 200–202 (methanol) | 1757 | (CDCl$_3$ + DMSO-d$_6$)1.43(s, 3H), 1.45(s, 3H), 1.92(m, 1H), 3.28(t, 2H, J=6.6Hz), 3.75(dd, 2H, J=5.1Hz, 12.2Hz), 4.04–4.16(m, 3H), 6.61 (d, 1H, J=7.3Hz), 6.74(d, 1H, J=10.5Hz), 10.71(br.s, 1H) |

EXAMPLE 34

5-Fluoro-6-[(tetrahydro-4H-pyran-3-yl)methylamino]-2-benzoxazolin-2-one

To a solution of 6-(5,6-dihydro-2H-pyran-3-yl)methylamino)-5-fluoro-2-benzoxazolone (1.0 g, 3.88 mmole) in 100 ml methanol was added 50 mg platinum oxide and the mixture was hydrogenated at 1 atm. and room temperature for 1 hour. The mixture was filtered, the filtrate concentrated in vacuo and the resulting solid was washed with ethanol. Recrystallization from ethanol gave 0.48 g of the title compound (47%): m.p. 177°–178° C.

IR (KBr): 1760, 1510, 1090, 950 cm$^{-1}$.

NMR: 1.15–1.30 (m, 1H), 1.35–1.65 (m, 2H), 1.75–1.90 (m, 2H), 2.90–2.95 (m, 2H), 3.05–3.15 (m, 1H), 3.70–3.85 (m, 2H), 5.25 (br, 1H), 6.75 (d, 1H), 6.89 (d, 1H), 11.30 (br, 1H).

EXAMPLE 35

5-Fluoro-6-[(tetrahydropyran-2-yl)methylamino]benzoxazolin-2-one

In a like manner, employing 5-fluoro-6-[(3,4-dihydro-2H-pyran-2-yl)methylamino]benzoxazolin-2-one in the procedure of Example 34 afforded the title compound: m.p. 185°–186° C.

IR (CH$_2$Cl$_2$): 3500, 1790, 1780 cm$^{-1}$.

NMR (CDCl$_3$): 1.36–1.67 (m), 1.89 (m, 1H), 3.04 (dd, 1H, J=8, 12 Hz), 3.16 (dd, 1H, J=3.5, 12 Hz), 3.42–3.61 (m, 2H), 4.03 (m, 1H), 4.27 (m, 1H), 6.62 (d, 1H, J=7.1 Hz), 6.78 (d, 1H, J=10.3 Hz), 8.52 (br.s, 1H).

EXAMPLE 36

5-Fluoro-6-[(1,2,3,4-tetrahydro-2-naphthyl)methylamino]benzoxazolin-2-one

In a manner similar to Example 3A starting with 5-fluoro-6-[(3,4-dihydro-2-naphthyl)methylamino]benzoxazolin-2-one but employing palladium carbon (5%) instead of platinum oxide, the title compound was prepared: m.p. 177°–178° C.

IR (KBr): 1770, 1660, 1520 cm$^{-1}$.

NMR: 1.30–1.50 (m, 1H), 1.90–2.10 (m, 2H), 2.49 (dd, 1H), 2.65–2.95 (m, 3H), 3.06 (dd, 2H), 5.36 (m, 2H), 6.79 (d, 1H), 6.93 (d, 1H), 11.21 (s, 1H).

EXAMPLE 37

5-Fluoro-6-[(chroman-3-yl)methylamino]benzoxazolin-2-one

In a manner similar to Example 34, starting with 5-fluoro-6-[(4-chloro-2H-chromene-3-yl)methylamino]benzoxazolin-2-one and hydrogenating it in the presence of triethylamine, the title compound was prepared: m.p. 223°–224° C.

IR (KBr): 1750, 1510, 1490 cm$^{-1}$.

NMR: 2.25–2.38 (m, 1H), 2.53–2.60 (m, 1H), 2.87 (dd, 1H), 3.06 (d, 1H), 3.09 (d, 1H), 3.87 (dd, 1H), 4.22–4.27 (m, 1H), 6.71–6.75 (m, 1H), 6.78–6.84 (m, 2H), 6.91 (d, 1H), 7.01–7.08 (m, 2H), 11.20 (br, 1H).

EXAMPLE 38

5-Methoxy-6-[(tetrahydropyran-3-yl)methylamino]benzoxazolin-2-one

Employing the procedure according to Example 34 with 5-methoxy-6-[(5,6-dihydro-2H-pyran-3-yl)methylamino]benzoxazolin-2-one afforded the title compound: m.p. 155° C (dec.).

IR (Nujol): 3200, 1780, 1740, 1680, 1640 cm$^{-1}$.

NMR: 1.20–1.25 (m, 1H), 1.42–1.60 (m, 2H), 1.72–1.91 (m, 2H), 2.87–2.94 (m, 2H), 3.08–3.15 (m, 1H), 3.69–3.81 (m, 6H), 6.58 (s, 1H), 6.62 (s, 1H), 11.09 (br.s, 1H).

EXAMPLE 39

5-Ethyl-6-[(tetrahydropyran-3-yl)methylamino]benzoxazolin-2-one

Employing the procedure according to Example 34 with 5-ethyl-6-[(5,6-dihydro-2H-pyran-3-yl)methylamino]benzoxazolin-2-one afforded the title compound: m.p. 148°–° C.

IR (Nujol): 3200, 2750, 1775, 1630 cm$^{-1}$.

NMR: 1.25–1.30 (m, 1H), 1.86–2.00 (m, 4H), 2.04 (s, 3H), 2.91–2.95 (m, 2H), 3.13–3.17 (m, 2H), 3.72 (br.s, 1H), 3.84 (br.s, 1H), 5.01–5.03 (m, 1H), 6.40 (s, 1H), 6.43 (s, 1H).

EXAMPLE 40

5-Fluoro-6-[(2,6-dimethyltetrahydropyran-3-yl)methylamino]benzoxazolin-2-one

Employing the procedure according to Example 34 with 5-fluoro-6-[(2,6-dimethyldihydro-2H-pyran-3-yl)methylamino]benzoxazolin-2-one afforded the title compound: m.p. 123°–139° C. (methanol).

IR (Nujol): 1757, 1788 cm$^{-1}$.

NMR (CDCl$_3$): 1.22 (d, 3H, J=6.1 Hz), 1.27 (d, 3H, J=6.6 Hz), 1.44 (m, 2H), 1.77 (m, 2H), 1.90–2.06 (m, 1H), 3.17–3.39 (m, 2H), 3.55 (m, 1H), 3.77 (m, 1H), 4.03 (br.s, 1H), 6.61 (d, 1H, 7.1 Hz), 6.79 (d, 1H, J=10.3 Hz), 8.70 (br.s, 1H).

EXAMPLE 41

5-Fluoro-6-[(tetrahydrothiopyran-3-yl)methylamino]benzoxazolin-2-one

Employing the procedure according to Example 34 with 5-fluoro-6-[(dihydro-2H-thiopyran-3-yl)methylamino]benzoxazolin-2-one afforded the title compound.

EXAMPLE 42

5-Fluoro-6-[(1-oxo-tetrahydrothiopyran-3-yl)methylamino]benzoxazolin-2-one

Alumina-supported sodium metaperiodate [K. T. Liu and Y. C. Tong, J.O.C. 43:2717 (1989)] (5.6 g) was added to a solution of 1.2 g (4.25 mmole) 5-fluoro-6-[(tetrahydrothiopyran-3-yl)methylamino]benzoxazolin-2-one in 200 ml ethanol and 50 ml THF. The mixture was stirred for 20 hours at room temperature. The alumina was filtered off and the solvent was removed in vacuo. The crude product was purified by silica gel column chromatography, eluting with ethyl acetate/THF/methanol (80:20:5), and recrystallized from methanol/diethyl ether to give the title compound (0.28 g, 22% yield).

IR (KBr): 1765, 1520, 1020, 940 cm$^{-1}$.

NMR: 1.1–1.25 (m, 1H), 1.4–1.55 (m, 1H of one isomer, E or Z at 1,3 position of tetrahydrothiopyran-1-oxide ring), 1.65–2.15 (m, 3H), 2.3–2.6 (m, 2H+1H of one isomer), 2.75–2.85 (m, 1H of one isomer), 2.9–3.15 (m, 2H of one isomer), 5.4–5.55 (m, 1H), 6.77–6.85 (m, 1H), 6.91 (d, 1H, J=10.6 Hz), 11.2 (br, 1H).

EXAMPLE 43

5-Fluoro-6-[3-(butylsulfinyl)propylamino]benzoxazolin-2-one

Employing the procedure according to Example 42 with 5-fluoro-6-[3-(butylthio)propylamino]benzoxazolin-2-one afforded the title compound: m.p. 116°–117° C. (methanol).

IR (CH$_2$Cl$_2$): 3480, 1780, 1660 cm$^{-1}$.

NMR: 0.90 (t, 3H, J=7.3 Hz), 1.40 (m, 2H), 1.60 (m, 2H), 1.91 (m, 2H), 2.57–2.88 (m, 4H), 3.18 (m, 2H), 5.38 (m, 1H), 6.79 (d, 1H, J=7.3 Hz), 6.90 (d, 1H, J=11.0 Hz), 11.23 (br.s, 1H).

EXAMPLE 44

R-5-Fluoro-6-[(tetrahydropyran-3-yl)methylamino]-benzoxazolin-2-one

To a solution of 5.04 g (30.0 mmol) of 6-amino-5-fluoro-benzoxazolin-2-one in 100 ml methanol was added 4.04 g of (S)-tetrahydropyran-3-yl-carboxaldehyde as an oil, prepared as described in Preparation L, below, at room temperature. Then, 4.0 ml acetic acid and 1.9 g (30.2 mmol) of sodium cyanoborohydride were added to the solution and the mixture was stirred for 1.5 hours. The solvent was evaporated down and water was added to the residue. The resulting solids were collected by filtration and dried at 50° C. under vacuum. Recrystallization of the crude product from methanol afforded 4.075 g of the title compound.

IR(CH$_2$Cl$_2$): 3500, 1790, 1780 cm$^{-1}$.

NMR(CDCl$_3$): 1.36–1.67 (m), 1.89 (m, 1H), 3.04 (dd, 1H, J=8, 12 Hz), 3.16 (DD, 1H, J=3.5, 12 Hz), 3.42–3.61 (m, 2H), 4.03 (m, 1H), 4.27 (m, 1H), 6.62 (d, 1H, J=7.1Hz), 6.78 (d, 1H, J=10.3 Hz), 8.52 (br.s, 1H).

EXAMPLE 45

S-5-Fluoro-6-[(tetrahydropyran-3-yl)methylamino]-benzoxazolin-2-one

Employing the procedure according to Example 44 with (R)-tetrahydropyran-3-yl-carboxaldehyde prepared as described in Preparation M, below, affords the title compound.

EXAMPLE 46

Starting with the appropriate aldehydes and variously substituted 6-amino-2-benzoxazolones and employing the procedure of Example 7, the following compounds are prepared:

![structure: R—(Alk)—NH— on benzoxazolin-2-one with R$_1$]

wherein Alk is (CH$_2$)$_n$

| n | R | R$_1$ |
|---|---|---|
| 0 | cyclohexyl | 5-CH$_3$O— |
| 1 | cyclohexyl | 5-CH$_3$O— |
| 1 | tetrahydropyranyl | 5-CH$_3$O— |
| 0 | cyclohexyl | H |
| 1 | tetrahydropyranyl | H |
| 1 | cyclohexyl | 4-CH$_3$— |
| 1 | cyclohexyl | 5-CF$_3$ |
| 2 | tetrahydropyranyl | 7-Cl |
| 2 | tetrahydropyranyl | phenoxy 5-position |
| 2 | CH$_3$—CH$_2$—CH$_2$—S— | 5-F |
| 2 | CH$_3$—CH$_2$—CH$_2$—S— | 5-F |
| 2 | CH$_3$—CH$_2$—CH$_2$—S— | 5-F |
| 3 | CH$_3$—CH$_2$—CH$_2$—S— | H |
| 1 | CH$_3$—CH$_2$—O— | 7-Cl |
| 1 | CH$_3$—CH$_2$—S— | 7-Cl |

PREPARATION A

6-Amino-5-fluorobenzoxazolin-2-one

A.1 4-Fluoro-2-nitrophenol

To a mechanically stirred solution of 400 ml concentrated nitric acid, at 0° C., was added dropwise a solution of 4-fluorophenol (204 g, 1.8 mole) in acetic acid (200 ml) over 2 hours. Stirring was continued for another 2 hours at 5° C. The reaction mixture was poured onto ice, and the resulting yellow solids were collected and washed with water. The solids were recrystallized from methanol-water (5:1) to afford 198 g of the title compound. The NMR spectrum showed absorption at 7.17 (dd, 1H, J=9, 5 Hz), 7.44–7.52 (m, 1H) and 7.80 (dd, 1H, J=8, 3 Hz).

A.2 2-Amino-4-fluorophenol

To a solution of 4-fluoro-2-nitrophenol (48.3 g, 0.30 mole) in 300 ml ethanol was added 0.24 g platinum oxide under nitrogen atmosphere. The mixture was hydrogenated with a Parr shaker for 8 hours at 45 psi. The catalyst was filtered off and the filtrate was concentrated to leave 40.5 g of the title compound as a brown powder. The NMR spectrum showed absorption at 4.79

(br.s, 2H), 6.11 (m, 1H), 6.36 (dd, 1H, J=11, 3 Hz), 6.53 (dd, 1H, J=5, 9 Hz) and 8.89 (s, 1H).

A.3 5-Fluorobenzoxazolin-2-one

To a solution of 2-amino-4-fluorophenol (40.5 g, 0.32 mole) in 400 ml tetrahydrofuran, at 0° C., was added dropwise trichloromethyl chloroformate (44.8 ml, 0.32 mole). The reaction mixture was allowed to warm up to room temperature Stirring was continued for 2 hours. Then, the reaction mixture was poured onto ice and the organic substance was extracted with ethyl acetate (500 ml×3). The combined extracts were washed with saturated sodium bicarbonate solution, dried over magnesium sulfate and concentrated to yield 44.3 g of the title compound as brown solids.

The NMR spectrum showed absorption at 6.86–6.90 (m, 1H), 7.01 (dd, 1H, J=8 3 Hz), 7.30 (dd, 1H, J=9, 5 Hz) and 11.82 (br.s, 1H).

A.4 5-Fluoro-6-nitrobenzoxazolin-2-one

To a stirred solution of 300 ml concentrated nitric acid, at room temperature, was added portionwise 73.2 g (0.48 mole) of 5-fluorobenzoxazolin-2-one. The reaction mixture was warmed to 50° C., and was stirred for 4 hours. After cooling, the reaction mixture was poured onto ice. The precipitate which formed was collected, washed with water, and dried to give 72.8 g of the title compound as a brown powder: m.p. 207°–209° C.

IR (Nujol): 3300, 1810, 1780, 1630 cm$^{-1}$.

NMR: 7.35 (d, 1H, J=11.0 Hz), 8.16 (d, 1H, J=6.6 Hz), 12.6 (br.s, 1H).

A.5 6-Amino-5-fluorobenzoxalin-2-one

To a solution of 5-fluoro-6-nitro-benzoxazolin-2-one (20 g, 0.1 mole) in 300 ml tetrahydrofuran was added 2 g palladium carbon (5%) under nitrogen atmosphere. The mixture was hydrogenated with a Parr shaker for 10 hours at 45 psi. The precipitate which resulted from hydrogenation was redissolved by adding tetrahydrofuran. The catalyst was removed by filtration and the filtrate was concentrated to give 18.1 g of the title compound as a brown solid: m.p. 180°–182° C. (dec.).

IR (Nujol): 3400, 3280, 1750, 1630 cm$^{-1}$.

NMR: 4.93 (br.s, 2H), 6.71 (d, 1H, J=7.3 Hz), 6.84 (d, 1H, J=10 Hz), 11.2 (br.s, 1H).

PREPARATION B

6-Amino-5-ethylbenzoxazolin-2-one

5-Ethyl-2-benzoxazolone was prepared via the condensation of 2-amino-4-ethylphenol with urea according to the procedure of W. J. Closs et al., J. Am. Chem. Soc., 71, 1265 (1949). In a manner similar to Preparation A, starting with 5-ethylbenzoxazolin-2-one, 6-amino-5-ethylbenzoxazol was prepared: m.p. 146°–147° C.

IR (Nujol): 3430, 3340, 3130, 1710, 1640 cm$^{-1}$.

NMR: 1.10 (t, 3H, J=7.3 Hz), 2.43 (q, 2H, J=7.3 Hz), 4.73 (br.s, 2H), 6.56 (s, 1H), 6.64 (s, 1H), 10.99 (br.s, 1H).

PREPARATION C

The procedure of Preparation A is employed to prepare 6-amino-4-methylbenzoxazolin-2-one, 6-amino-5-methylbenzoxazolin-2-one, 6-amino-5-trifluoromethylbenzoxazolin-2-one, 6-amino-5-methoxybenzoxazolin-2-one, -amino-5-methylthiobenzoxazolin-2-one, 6-amino-5-phenoxybenzoxazolin-2-one, 6-amino-5-phenylthiobenzoxazolin-2-one, 6-amino-7-chlorobenzoxazolin-2-one and 6-amino-7-fluorobenzoxazolin-2-one.

PREPARATION D

3-(Tetrahydropyran-3-yl)propionaldehyde

D.1 Ethyl-3-(5,6-dihydro-2H-pyran-3-yl)acrylate

To a stirred suspension of sodium hydride (60% in mineral oil; 1.43 g, 35.7 mmoles) in 50 ml tetrahydrofuran, at room temperature, was added dropwise triethyl phosphonoacetate (8.35 g, 37.2 mmoles) under a nitrogen atmosphere. The reaction mixture was stirred for 15 minutes. To this was added dropwise a solution of 3.34 g (29.8 mmoles) of 3-formyl-5,6-dihydro-2H-pyrane (Japan Kokai 59-167,584 to BASF) in 20 ml tetrahydrofuran. The resulting mixture was stirred for 1 hour. The reaction was quenched by adding acetic acid. Then, the reaction mixture was concentrated and an aqueous sodium bicarbonate solution was added. The organic substance was extracted with ethyl acetate The extract was washed with brine, dried over magnesium sulfate and evaporated to an oil. The crude oil was purified by column chromatography on silica gel eluted with 25% ethyl acetate-hexane to yield 3.1 g of the title compound.

The NMR spectrum showed absorption at 1.26–1.38 (m, 3H), 2.34 (br., 2H), 3.8 (t, 2H, J=5 Hz), 4.15–4.30 (m, 4H), 5.63 (d, 1H, J=17 Hz), 6.28 (br., 1H) and 7.21 (d, 1H, J=17 Hz).

D.2 Ethyl-3-(tetrahydro-2H-pyran-3-yl)propionate

A solution of ethyl-3-(5,6-dihydro-2H-pyran-3-yl) acrylate (3.1 g) in 50 ml methanol was hydrogenated over 0.15 g of palladium carbon (5%) at room temperature under a hydrogen atmosphere. The catalyst was removed by filtration and the filtrate was concentrated to yield a crude oil. The crude product was purified by column chromatography on silica gel eluted with 50% ethyl acetate-hexane to give 3.0 g of the title compound.

The NMR spectrum showed absorption at 1.10–1.20 (m, 1H), 1.26 (t, 3H, J=7 Hz), 1.45–1.63 (m, 5H), 1.82–1.91 (m, 1H), 2.27–2.34 (m, 2H), 3.06 (dd, 1H, J=9.5, 11 Hz), 3.30–3.40 (m, 1H), 3.83–3.89 (m, 2H) and 4.13 (q, 2H, J=7 Hz).

D.3 3-(Tetrahydro-2H-pyran-3-yl)propionaldehyde

To a solution of ethyl-3-(tetrahydro-2H-pyran-3-yl)propionate (3.0 g) was, at −78° C., added dropwise DIBAL (16 ml of 1.5 mole toluene solution) under a nitrogen atmosphere. Stirring was continued for one hour. The reaction was quenched by adding a methanol-water mixture. The resulting solution was allowed to warm up to room temperature. The solids which formed were removed. The filtrate was dried over magnesium sulfate and concentrated to yield a crude oil. The crude product was purified by distillation to yield 2.0 g of the title compound.

The NMR spectrum showed absorption at 1.09–1.28 (m, 1H), 1.42–1.65 (m, 5H), 1.80–1.91 (m, 1H), 2.42–2.49 (m, 2H), 3.07 (dd, 1H, J=9, 11 Hz), 3.31–3.40 (m, 1H), 3.84–3.89 (m, 2H) and 9.78 (s, 1H).

PREPARATION E

3-Methylcyclohexanecarboxaldehyde

E.1 3-Methylcyclohexanecarboxylic acid

To a solution of m-toluic acid (13.6 g, 0.1 mole) in acetic acid was added platinum oxide (0.1 g) under nitrogen. The mixture was hydrogenated in a Parr shaker at 35 psi. Upon completion, the catalyst was removed by filtration and the filtrate was concentrated to dryness to give 12 g of the title compound. The NMR spectrum showed absorption at 0.84 (d, 3H), 0.90 (d, 3H), 0.99–1.13 (m, 1H), 2.21–1.46 (m, 3H), 1.54–1.65 (m, 3H), 1.70–1.98 (m, 2H) and 1.23–2.41 (m, 1H).

E.2 1-Hydroxymethyl-3-methylcyclohexane

To a boran-methyl sulfide complex (1.7 ml, 0.028 mole) in 7 ml tetrahydrofuran, at 0° C., was added dropwise 2 g of 3-methylcyclohexanecarboxylic acid (0.014 mole) in 7 ml tetrahydrofuran. Stirring was continued for one hour. The reaction mixture was diluted with ether and washed with 1N aqueous sodium hydroxide and then with brine. Concentration and distillation gave 1.34 g of the title compound The NMR spectrum showed absorption at 0.54–0.74 (m, 1H), 0.90, 0.93 (s, 3H), 1.17–1.53 (m, 3H), 1.65–1.77 (m, 3H) and 3.39–3.52 (m, 2H).

E.3 3-Methylcyclohexanecarboxaldehyde

To a solution of 1-hydroxymethylcyclohexane (6.8 g, 0.053 mole) in 150 ml dichloromethane was added pcc (22.9 g, 0.106 mole) under nitrogen. Stirring continued for 1 hour at room temperature. The solids were removed by filtration through Florisil and the filtrate was concentrated to give 8 g of the title compound. The NMR spectrum showed 0.90, 0.95 (d, 3H, J=8 Hz), 0.86–2.32 (m, 10H), and 9.68, 9.70 (d, 1H, J=2 Hz).

PREPARATION F

Endo-7-Oxabicyclo(2,2,1)heptane-2-carboxaldehyde

Using the procedure of Preparation D3 endo-2-carbomethoxy-7-oxabicyclo(2,2,1)heptane (M. P. Kunstmann et al., J. Am. Chem. Soc., 84, 4115 (1962); 2.13 g, (12.5 mmoles) was reduced to the title compound (1.51 g).

The NMR spectrum showed absorption at 1.46–1.95 (m, 6H), 3.07 (m, 1H), 4.68 (m, 1H), 4.86 (dd, 1H, J=5.6, 5.6 Hz) and 9.73 (d, 1H, J=1.5 Hz). In like manner exo-2-carbomethoxy-7-oxabicyclo(2,2,1)heptane was reduced to the corresponding exo-7-oxabicyclo(2,2,1)heptane-2-carboxaldehyde.

PREPARATION G

5-Fluoro-6-[(4-chloro-2H-chromen-3-yl)methylamino]-benzoxazolin-2-one

G.1 4-Chloro-3-formyl-2H-chromene

The title compound was prepared according to the procedure of J. A. Vigilio et al., Organic Preparations and Procedures Inc., 14, 9 (1982).

G.2
5-Fluoro-6-[(4-chloro-2H-chromen-3-yl)methylamino]-benzoxazolin-2-one

To a solution of 6-amino-5-fluorobenzoxazolin-2-one (2.02 g, 12 mmole) in ethanol (100 ml) was combined the product of G.1 (2.53 g, 13 mmole). The mixture was stirred at room temperature for 6 hours. The reaction mixture was then concentrated in vacuo to yield solids. The solid product was washed with ethanol. This product was dissolved in methanol (150 ml) and sodium borohydride was added in portions at room temperature. Stirring was continued for hours. The reaction mixture was concentrated and aqueous ammonium chloride was added. The organic material was extracted with ethyl acetate/THF. The combined extracts were washed with brine, dried over magnesium sulfate and concentrated. The residue was chromatographed on silica gel, eluted with ethyl acetate/hexane (1:3) to afford the crude product, which was recrystallized from ethanol to give 0.90 g of the title compound (22%): m.p. 197° C. (dec.).

PREPARATION H

6-Oxabicyclo[3.2.1]oct-1′-ylmethanol

H.1 6-Oxabicyclo[3.2.1]oct-1′-ylmethanol

A mixture of 3-cyclohexene-1,1-dimethanol (10.0 g, 70 mmol; Aldrich Chemical Company, Inc.) and NBS (13.7 g, 77 mmol) in 200 ml dichloromethane was stirred for 13 hours at room temperature. Then, the reaction mixture was washed with water (2×100 ml) and brine and dried over Na$_2$SO$_4$. The solvent was removed by evaporation to give a pale yellow oil (17.0 g). To a mixture of this oil and 20 ml toluene were added ALBN (0.2 g) and then n-tributyltinhydride (21.5 g, 84 mmol) with stirring. The mixture was heated to 110° C. and stirred for 1.5 hours. Silica gel chromatography of the product (150 g, 50% ethyl acetate/hexane, twice) gave the title compound (7.75 g, 77% yield).

The NMR spectrum (CDCl$_3$) showed absorption at 1.28–1.52 (m, 3H), 1.66–1.84 (m, 6H), 3.57 (dd, 2H, J=1.84 Hz, 5.50 Hz), 3.65 (dd, 1H, J=1.84 Hz, 7.69 Hz), 3.84 (d, 1H, J=7.69 Hz), 4.40 (t, 1H, J=5.31 Hz).

H.2 6-Oxabicyclo[3.2.1]oct-1′-ylcarboxaldehyde

A mixture of 6-oxabicyclo[3.2.1]oct-1′-ylmethanol (3.55 g, 25 mmol), pcc (8.08 g, 37.5 moles) and 100 ml dichloromethane was stirred at room temperature for one hour. The resulting mixture was diluted with 100 ml diethylether and filtered through silica gel. The silica gel was washed with diethylether (7×100 ml). The filtrate and washings were combined, the solvent was removed by evaporation to give the title compound (3.00 g, 86% yield).

The NMR spectrum (CDCl$_3$) showed absorption at 1.29–1.40 (m, 1H), 1.57–1.90 (m, 6H), 2.19–2.26 (m, 1H), 3.89 (d, 1H, J=8.4 Hz), 4.03 (dd, 1H, J=1.8 Hz, 8.4 Hz), 4.53 (dd, 1H, J=4.8 Hz, 5.9 Hz), 9.56 (s, 1H).

PREPARATION I (1S,2R,4R)-7-oxabicyclo[2.2.1]heptan-2-carboxaldehyde

I.1
(4S)-3-[(1S,2R,4R)-7-oxabicyclo[2.2.1]hept-2-ylcarbonyl]-4-isopropyloxazolidin-2-one and
(4S)-3-[(1R,2S,4S)-7-oxabicyclo[2.2.1]hept-2-ylcarbonyl]-4-isopropyloxazolidin-2-one A stirred, cooled (−78° C.) solution of 7.75 g (60 mmol) of (4S)-4-isopropyloxazolidin-2-one in 200 ml of THF was metalated with 44 ml of n-butyllithium (1.49M in hexane, 65 mmol). To the reaction was then added racemic exo-oxabicyclo[2.2.1]heptan-2-carboxyl chloride prepared from 8.95 g (63 mmol) of the corresponding racemic acid and oxalyl chloride. The reaction mixture was warmed to 0° C. and stirred for one hour. Excess acid chloride was hydrolyzed by the addition of 50 ml of 1M aqueous potassium carbonate followed by stirring of the mixture for one hour at room temperature. Organic solvent was removed under reduced pressure. The resulting product was diluted with 200 ml of water and extracted with dichloromethane (4×200 ml). The combined organic extracts were successively washed with water (200 ml) and brine (200 ml), dried over anhydrous magnesium sulfate and concentrated in vacuo to give 18.0 g of a pale yellow oil. Separation of the diastereomeric imides was accomplished on a Waters Prep LC/System 500A using two Prep-PAK-500/silica cartridges (57 mm×30 cm, ether/n-hexane (1:5), flow rate 250 ml/min.) in three runs. The retention times of the less polar imide and the more polar imide were 16 and 22 minutes, respectively. The less polar imide (6.47 g), which contained an unknown impurity, was purified by recrystallization from ether-hexane to give 4.47 g (29% yield) of the pure, less polar imide, (4S)-3-[(1S,2R,4R)-7-oxabicyclo[2.2.1]hept-2-ylcarbonyl]-4-isopropyloxazolidin-2-one, (>99% de). The structure of the less polar imide was determined by X-ray analysis using crystal obtained by another slow recrystallization from ether-hexane. The more polar imide (4S)-3-[(1R,2S,4S)-7-oxabicyclo[2.2.1]hept-2-ylcarbonyl]-4-isopropyloxazolidin-2-one, (6.36 g, 42% yield, 98.5% de) was used without further purification.

I.2
Methyl(1S,2R,4R)-7-oxabicyclo[2.2.1]heptan-2-carboxylate

To a cooled (0° C.) solution of (4S)-3-[(1S,2R,4R)-7-oxabicyclo[2.2.1]hept-2-ylcarbonyl]-4-isopropyloxazolidin-2-one (4.35 g, 17 mmol) in 350 ml of THF was added slowly and dropwise, with stirring, an aqueous lithium hydrogen peroxide solution (prepared from 15 ml of 30% aqueous hydrogen peroxide, 1.28 g (30 mmol) of lithium hydroxide and 120 ml of water). After stirring for one hour at 0° C., the reaction was quenched by dropwise addition of 300 ml of 2N sodium sulfite. After stirring the resulting slurry for 15 minutes at 0° C., the mixture was basified with saturated sodium bisulfite and the organic solvent was removed in vacuo. The remaining aqueous mixture was washed with 200 ml of dichloromethane After acidification with concentrated HCl, the chiral acid was extracted ten times with 300 ml of dichloromethane. The combined organic phases were dried over magnesium sulfate and concentrated in vacuo to give the unpurified acid as a pale-yellow oil. The unpurified acid was diluted with 100 ml of ether and treated with excess diazomethane in ether. After 15 minutes, the excess diazomethane was removed by bubbling nitrogen through the solution. The resulting solution was concentrated under reduced pressure and purified by flash chromatography [100 g of silica gel, ether/hexane (1:1)] to give 2.03 g (76% yield) of the title compound as a clear volatile oil. An analytical sample was purified by Kugelrohr distillation: b.p. 106°-109° C./0.9 mm Hg.

IR (Nujol): 3000, 2970, 2880, 1736, 1064, 1002, 938 cm$^{-1}$.

NMR (CDCl$_3$): 1.42-1.55 (m, 2H), 1.67-1.80 (m, 3H), 2.09-2.17 (m, 1H), 2.61 (dd, 1H, J=4.9 Hz, 9.1 Hz), 3.70 (s, 3H), 4.66 (dd, 1H, J=4.9 Hz, 5.1 Hz), 4.84 (d, 1H, J=4.9 Hz).

$[\alpha]_D^{20}$: +31 3° (c1.00, methanol).

I.3
(1S,2R,4R)-7-oxabicyclo[2.2.1]heptan-2-carboxaldehyde

Using the procedure of Preparation D.3, methyl (1S,2R,4R)-7-oxabicyclo[2.2.1]heptan-2-carboxylate was converted to the title compound. The NMR spectrum (CDCl$_3$) showed absorption at 1.46-1.95 (m, 6H), 3.07 (m, 1H), 4.68 (m, 1H), 4.86 (dd, 1H, J=5.6 Hz, 5.6 Hz), 9.73 (d, 1H, J=1.5 Hz).

PREPARATION J
(1R,2S,4S)-7-oxabicyclo[2.2.1]heptan-2-carboxaldehyde

J.1
Methyl(1R,2S,4S)-7-oxabicyclo[2.2.1]heptan-2-carboxylate

Employing the procedure according to Preparation I.2 with (4S)-3-[(1R,2S,4S)-7-oxabicyclo[2.2.1]hept-2-ylcarbonyl]-4-isopropyloxazolidin-2-one afforded the title compound (96% yield): b.p. 94°-98° C./0.5 mm Hg.

IR (Nujol): 3000, 2970, 2880, 1736, 1064, 1002, 938 cm$^{-1}$.

NMR (CDCl$_3$): 1.42-1.55 (m, 2H), 1.67-1.80 (m, 3H), 2.09-2.17 (m, 1H), 2.61 (dd, 1H, J=4.9 Hz, 9.1 Hz), 3.70 (s, 3H), 4.66 (dd, 1H, J=4.9 Hz, 5.1 Hz), 4.84 (d, 1H, J=4.9 Hz).

$[\alpha]_D^{20}$: −29.8° (c1.00, methanol).

J.2
(1R,2S,4S)-7-oxabicyclo[2.2.1]heptan-2-carboxaldehyde

Using the procedure of Preparation D.3, methyl (1R,2S,4S)-7-oxabicyclo[2.2.1]heptan-2-carboxylate was converted to the title compound. The NMR spectrum (CDCl$_3$) showed absorption at 1.46-1.95 (m, 6H), 3.07 (m, 1H), 4.68 (m, 1H), 4.86 (dd, 1H, J=5.6 Hz, 5.6 Hz), 9.73 (d, 1H, J=1.5 Hz).

PREPARATION K
2-Oxabicyclo[2.2.1]hept-4-ylmethanol

To a mixture of 3-cyclopenten-1,1-dimethanol, prepared according to J-P. Déprés, et al., J. Org. Chem. 49:928 (1984) and H. Paulsen, et al., Chem. Ber. 144:346 (1981), (3.74 g, 29 mmol), 100 ml of dichloromethane and 100 ml THF was added NBC (5.71 g, 32 mmol) with stirring at 0° C. After addition of NBS was completed, the ice-bath was removed and the reaction mixture was stirred at room temperature. After 2.5 hours, another portion of NBS (5.71 g, 32 mmol) was added and the reaction mixture was stirred for an additional one hour at room temperature. The reaction mixture was then partitioned between 200 ml of CHCl$_3$ and 200 ml of water. The aqueous phase was extracted with 100 ml CHCl$_3$. The combined organic phases were washed with 0.5N Na$_2$SO$_4$ and then with brine, dried over MgSO$_4$ and evaporated. The residual oil was applied to a silica gel column (150 g) and eluted with 33% ethyl acetate/hexane to about 50% ethyl acetate/hexane. Fractions containing the desired product as a main component were combined. Evaporation of the solvent gave 3.47 g of a pale yellow oil. A mixture of the oil, tri-n-butyltinhydride (5.44 g, 18.7 mmol), ALBN (0.05 g) and 4 ml toluene was refluxed for 80 minutes. Silica gel column chromatography (150 g, 50% ethyl acetate/hexane to about 67% ethyl acetate/hexane) gave the title compound (1.10 g).

The NMR spectrum (CDCl$_3$) showed absorption at 1.41 (d, 1H, J=9.5 Hz), 1.54-1.79 (m, 5H), 3.67 (dd, 1H, J=2.8 Hz, 6.8 Hz), 3.83 (s, 2H), 4.36 (s, 1H).

PREPARATION L

(S)-Tetrahydropyran-3-yl-carboxaldehyde

L.1 Diethyl(2S,3R)-3-allyl-2-hydroxysuccinate

Employing the procedures of D. Seebach et al., Helv. Chim. Act. 60: 301 (1979) and D. Seebach et al., Org. Synth. 63: 109 (1985) and starting with S-malic acid allylation was carried out with allylbromide on a 34 g scale. The resulting diastereomeric mixture (3:4=10:1) was purified by medium pressure column chromatography using 1 kg of silica gel and 15% ethyl acetate/hexane. The same scale reaction was repeated and the impure fraction from both were combined and purified again using the same chromatographic procedure to yield 35.06 g (43%) of the anti-diastereomer diethyl (2S,3R)-3-allyl-2-hydroxysuccinate.

L.2 (2S,3S)-3-Allyl-2-(methoxymethyl)oxy-1,4-butanediol

To a solution of 21.78 g (94.7 mmol) of diethyl (2S,3R)-3-allyl-2-hydroxysuccinate in 500 ml methylal were added 15 g molecular sieves 4A and 5.23 g Amberlyst 15. To the reaction vessel was attached an addition funnel containing 150 ml of molecular sieves 4A. The reaction mixture was heated at reflux. After 4 hours, the molecular sieves 4A in the funnel were replaced with 150 ml of fresh molecular sieves 4A and heating of the reaction was continued for an additional 4 hours. The reaction mixture was filtered through Celite and concentrated in vacuo to provide 25.34 g of the diethyl ester in the MOM protected form. The MOM-protected diethyl ester was slowly added to a suspension of LAH (4.90 g, 129 mmol) in 500 ml tetrahydrofuran at room temperature. The addition was controlled so as to maintain the reaction temperature at around 35° C. After the addition was completed, stirring was continued for 1 hour. Then, the reaction was quenched with wet tetrahydrofuran followed by addition of a saturated aqueous solution of Rochelle salt. The reaction mixture then was filtered through Celite and the filtrate was concentrated in vacuo to afford 17.2 g of the corresponding MOM-protected diol, (2S,3S)-3-allyl-2-(methoxymethyl)oxy-1,4-butanediol. Using the above described procedures in another run, 12.41 g of (2S,3S)-3-allyl-2-(methoxymethyl)oxy-1,4-butanediol was obtained from 15.99 g of the starting diethyl ester. The (2S,3S)-3-allyl-2-(methoxymethyl)oxy-1,4-butanediol obtained from the two runs were combined and purified by medium pressure column chromatography using 1 kg silica gel, 66% ethylacetate/hexane, 100% ethyl acetate, to yield 24.11 g of (2S,3S)-3-allyl-2-(methoxymethyl)oxy-1,4-butanediol.

L.3 (2S,3S)-2-(Methoxymethyl)oxy-3-(3-tosyloxypropyl)-1,4-butanediol dibenzoate To a solution of 22.13 g (116 mmol) of (2S,3S)-3-allyl-2-(methoxymethyl)oxy-1,4-butanediol in 100 ml pyridine was added 27.5 ml (237 mmol) of benzoyl chloride at room temperature. The reaction was exothermic and was completed in 1 hour. Most of the solvent was removed under vacuum, and the residue was acidified with diluted HCL (1N) and extracted with ether. The organic phase was washed with aqueous sodium bicarbonate and brine and then dried over sodium sulfate. Evaporation of the solvent yielded 47.8 g of the corresponding crude dibenzoate. The crude dibenzoate was azeotropically dried with benzene and dissolved in 360 ml of tetrahydrofuran. Then, 9.0 ml (10.0M) of boranemethylsulfide complex was added to the solution at 5° C. and then the mixture was stirred at room temperature for 2 hours. The reaction was then quenched with methanol and 21.5 g (286 mmol) of trimethylamine N-oxide dihydrate was added. The solvent was replaced by 400 ml of xylene and the solution was heated at reflux for 20 minutes. The reaction mixture then was diluted with ether, washed with brine and dried over sodium sulfate. The solvent was evaporated under vacuum to afford the corresponding alcohol which was combined with the alcohol obtained from another run starting with 1.98 g (10.4 mmol) of (2S,3S)-3-allyl-2-(methoxymethyl)oxy-1,4-butanediol. In 400 ml of methylene chloride were dissolved the combined alcohol produced above, 24.5 g (138 mmol) p-toluenesulfonyl chloride and 53 ml (380 mmol) triethylamine. Then, 1.62 g (13.3 mmol) of 4-dimethylaminopyridine was added to the solution and the reaction mixture was stirred overnight. The resultant mixture was partitioned between water and ether and the organic phase was washed with brine and dried over sodium sulfate. The solvent was evaporated and the crude residue was subjected to medium pressure column chromatography using silica-gel and 28% ethyl acetate/hexane to afford 47.3 g of (2S,3S)-2-(methoxymethyl)oxy-3-(3-tosyloxypropyl)-1,4-butanediol dibenzoate.

L.4 (2S)-2-[(3S)-Tetrahydropyran-3-yl]-2-(methoxymethyl)oxyethanol

In 600 ml of tetrahydrofuran, containing 3.3 ml methanol were dissolved 47.3 g (82.3 mmol) of (2S,3S)-2-(methoxymethyl)oxy-3-(3-tosyloxypropyl)-1,4-butanediol dibenzoate and the solution was chilled in an ice-bath. To the solution were added, portionwise, 20.65 g (184 mmol) of potassium t-butoxide and the reaction mixture was stirred at room temperature for 2.5 hours. Then, an additional 2.46 g (22 mmol) of potassium t-butoxide and 150 µl of water were added and the reaction was stirred for an additional 30 minutes. Finally, 6 ml of water was added and the mixture was further stirred for 2 hours. The reaction mixture then was poured into a mixture of water and ethyl acetate. The aqueous phase was extracted four times with ethyl acetate and twice with 10% isopropanol-methylene chloride. The organic extracts were combined, dried over magnesium sulfate, carefully concentrated and purified by medium pressure column chromatography using silica gel and 72% ethyl acetate/hexane, 100% ethylacetate. The resulting compound, (2S)-2-[(3S)-tetrahydropyran-3-yl]-2-(methoxymethyl)oxyethanol, was found to be volatile. Thus, evaporation of the solvent was carefully carried out with an aspirator below room temperature. Pure fractions were collected and combined to yield 9.82 g of (2S)-2-[(3S)-tetrahydropyran-3-yl]-2-(methoxymethyl)oxyethanol contaminated with ethyl acetate (34%) as judged by 270 MHz $^1$H-NMR.

L.5. (S)-Tetrahydropyran-3-yl-carboxaldehyde

To a solution of 8.7 g (33 mmol, 66% purity) of (2S)-2-[(3S)-tetrahydropyran-3-yl]-2-(methoxymethyl)oxyethanol in 77 ml of water and 6.0 ml methanol was added 8.0 g of Amberlyst 15. The resultant mixture was heated at 65° C. with stirring for 1 hour. The Amberlyst 15 was removed by filtration through Celite and washed with ether and methanol. Then, most of the ether and methanol in the filtrate were distilled off at atmospheric pressure and the residual water was azeotropically removed with benzene. The resulting solution was concentrated down to about 200 ml and 16.3 g (33.1 mmol, 90% purity) of lead tetraacetate was added to the solution cooled in an ice-bath. The reaction mixture was warmed to room temperature and stirred for 45 minutes. Then, insoluble materials were removed from the reaction mixture by filtration through Celite. The solvent was carefully evaporated off the filtrate and the residual oil was distilled at 20 mmHg. The fraction which boiled at 60°–80° C. was collected to yield 4.04 g of (S)-tetrahydropyran-3-yl-carboxaldehyde which was contaminated with a trace amount of acetic acid and benzene as judged by $^1$H-NMR.

NMR(CDCl$_3$): 1.45–1.91 (m, 4H), 2.34–2.43 (m, 1H), 3.47 (d.d.d., 1H, J=11.5, Hz), 3.63 (d.d.d., 1H, J=11.3, 6.5, 3.9 Hz), 3.72 (d.d., 1H, J=11.7, 6.8 Hz), 3.88 (d.d., 1H, J=11.7, 3.2 Hz), 9.62 (s, 1H).

PREPARATION M (R)-Tetrahydropyran-3-yl -carboxaldehyde

Employing the procedures according to Preparation L, above, and starting with R-malic acid instead of S-malic acid affords (R)-tetrahydropyran-3-yl-carboxaldehyde.

What is claimed is:

1. A compound of the formula:

or a pharmaceutically-acceptable acid addition salt thereof, wherein Alk is a $C_n$ straight or branched chain divalent alkyl group; n is 1, 2, 3, 4, or 5;

$R_1$ is $(C_1-C_3)$alkyl, $(C_1-C_3)$alkoxy, $(C_1-C_3)$alkylthio, hydrogen, halo, phenoxy, phenylthio or trifluoromethyl; and R is selected from the group consisting of:

(a)

wherein $R_2$ and $R_3$ are each, independently, H, $(C_1-C_4)$alkyl, $(C_1-C_4)$alkoxy, $(C_1-C_4)$alkylthio or halo, X is methylene which is unsubstituted or substituted with one methyl group, nitrogen which is unsubstituted or substituted with a protecting group, oxygen, sulfur, sulfoxide or sulfone, and the dotted line between the 2- and 4- positions represents an optional bond between positions 2 and 3 or positions 3 and 4;

(b)

wherein A and B are each, independently, O or S;

(c)

(d)

wherein $R_4$ and $R_5$ are each, independently, H or $(C_1-C_4)$alkyl, p is 0, 1 or 2 and t is 0, 1 or 2 provided that the sum of p plus t equals 1 or 2; and the wavy line indicates that the moiety containing such wavy line can be endo- or exo-7-oxabicyclo[2,2,1-]heptan-1-yl; and (e) $CH_3-(CH_2)_m-Y-$ wherein m is an integer from 1 to 3 and Y is oxygen, sulfur, sulfoxide or sulfone.

2. A compound according to claim 1 or a pharmaceutically-acceptable acid addition salt thereof wherein n is 1, $R_1$ is 5-halo and R is

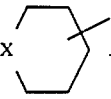

3. A compound according to claim 2 or a pharmaceutically-acceptable acid addition salt thereof wherein $R_1$ is 5-fluoro and X is oxygen.

4. A compound according to claim 1 or a pharmaceutically-acceptable acid addition salt thereof wherein

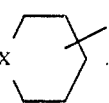

n is 1, $R_1$ is 5-$(C_1-C_3)$alkyl or $(C_1-C_3)$alkoxy and R is

5. A compound according to claim 4 or a pharmaceutically-acceptable acid addition salt thereof wherein $R_1$ is 5-ethyl and X is oxygen.

6. A compound according to claim 1 or a pharmaceutically-acceptable acid addition salt thereof wherein n is 1, 2, 3, 4 or 5, $R_1$ is halo and R is a member selected from Group (b).

7. A compound according to claim 1 or a pharmaceutically-acceptable acid addition salt thereof wherein n is 1, $R_1$ is 5-fluoro and R is a member selected from Group (c).

8. A compound according to claim 1 or a pharmaceutically-acceptable acid addition salt thereof wherein n is 1, $R_1$ is 5-fluoro and R is a member selected from Group (d).

9. A compound according to claim 1 or a pharmaceutically-acceptable acid addition salt thereof wherein n is 1, 2, 3, 4 or 5, $R_1$ is 5-halo and R is a member selected from Group (e).

10. A compound according to claim 9 or a pharmaceutically-acceptable acid addition salt thereof wherein $R_1$ is 5-fluoro, m is 1 and Y is oxygen or sulfur.

11. A compound according to claim 1 or a pharmaceutically-acceptable acid addition salt thereof wherein $R_1$ is $(C_1-C_3)$alkoxy and R is a member selected from Group (a).

12. A compound according to claim 11 wherein $R_1$ is methoxy, n is 1 and X is oxygen.

13. The compound 5-fluoro-6-[(tetrahydropyran-3-yl)methylamino]benzoxazolin-2-one according to claim 3 or a pharmaceutically-acceptable acid addition salt thereof.

14. The compound R-5-fluoro-6-[(tetrahydropyran-3-yl)methylamino]benzoxazolin-2-one according to claim 13 or a pharmaceutically-acceptable acid addition salt thereof.

15. The compound S-5-fluoro-6-[(tetrahydropyran-3-yl)methylamino]benzoxazolin-2-one according to claim 13 or a pharmaceutically-acceptable acid addition salt thereof.

16. The compound 5-fluoro-6-[(6-oxabicyclo[3.2.1]octyl-1-yl)methylamino]benzoxazolin-2-one according to claim 8 or a pharmaceutically-acceptable acid addition salt thereof.

17. The compound 5-fluoro-6-[(7-oxabicyclo[2.2.1]hept-2-yl)methylamino]benzoxazolin-2-one according to claim 8 or a pharmaceutically-acceptable acid addition salt thereof.

18. The compound 5-fluoro-6-[[(1S,2R,4R)-7-oxabicyclo[2.2.1]hept-2-yl)methylamino]benzoxazolin-2-one according to claim 8 or a pharmaceutically-acceptable acid addition salt thereof.

19. The compound 5-fluoro-6-[[(1R,2S,4S)-7-oxabicyclo[2.2.1]hept-2-yl)methylamino]benzoxazolin-2-one according to claim 8 or a pharmaceutically-acceptable acid addition salt thereof.

20. A method for treating an allergic condition in a mammal which comprises administering to such mammal an allergic condition treating amount of a compound according to claim 1 or a pharmaceutically-acceptable acid addition salt thereof.

21. A method for treating an inflammatory condition in a mammal which comprises administering to such mammal an inflammatory condition treating amount of a compound according to claim 1 or a pharmaceutically-acceptable acid addition salt thereof.

22. A pharmaceutical composition useful in treating an allergic or inflammatory condition in a mammal which comprises an effective amount of a compound according to claim 1 or a pharmaceutically-acceptable acid addition salt thereof and a pharmaceutically-acceptable carrier or diluent.

* * * * *

UNITED STATES PATENT AND TRADEMARK OFFICE
CERTIFICATE OF CORRECTION

PATENT NO. : 5,086,062

DATED : February 4, 1992

INVENTOR(S) : Kazuo Ando et al.

It is certified that error appears in the above-identified patent and that said Letters Patent is hereby corrected as shown below:

On the title page under Related U.S. Application Data, "Feb. 12, 1990" should read -- Feb. 22, 1990 --;

At Column 15, line 67, "148°-°C." should read -- 148°-150°C. --;

At Column 19, line 66, "-amino-5-methylthiobenzoxazolin-2-one" should read -- 6-amino-5-methylthiobenzoxazolin-2-one --;

At Column 24, line 53, "$Na_2SO_4$" should read -- $Na_2S_2O_3$ --;

At Column 27, line 16, "(d.d.d., 1H, J=11.5, Hz)," should read -- (d.d.d., 1H, J=11.5, 7.6, 3.7 Hz), --;

At Column 28, lines 50-55, " " should read --  --; and

UNITED STATES PATENT AND TRADEMARK OFFICE
CERTIFICATE OF CORRECTION

PATENT NO. : 5,086,062
DATED : February 4, 1992
INVENTOR(S) : Kazuo Ando et al.

It is certified that error appears in the above-identified patent and that said Letters Patent is hereby corrected as shown below:

At Column 28, lines 61-68, "wherein 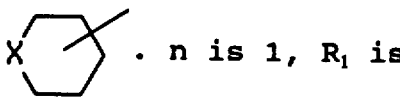 . n is 1, $R_1$ is 5-$(C_1-C_3)$alkyl or $(C_1-C_3)$alkoxy and R is" should read -- wherein n is 1, $R_1$ is 5-$(C_1-C_3)$alkyl or $(C_1-C_3)$alkoxy and R is  . --

Signed and Sealed this

Thirty-first Day of May, 1994

Attest:

BRUCE LEHMAN

Attesting Officer

Commissioner of Patents and Trademarks